United States Patent

Ruess

[11] Patent Number: 5,780,469
[45] Date of Patent: Jul. 14, 1998

[54] CROP PROTECTION PRODUCTS

[75] Inventor: Wilhelm Ruess, Pfeffingen, Switzerland

[73] Assignee: Novartis Finance Corporation, New York, N.Y.

[21] Appl. No.: 761,543

[22] Filed: Dec. 6, 1996

[30] Foreign Application Priority Data

Dec. 11, 1995 [CH]  Switzerland ............... 3495/95

[51] Int. Cl.[6] .................. A01N 43/82; A61K 31/535
[52] U.S. Cl. .................. 514/237.5; 514/361
[58] Field of Search .................. 514/237.5, 361

[56] References Cited

U.S. PATENT DOCUMENTS 5,190,928  3/1993  Schurter et al. ............... 514/63

FOREIGN PATENT DOCUMENTS

WO 9622690  8/1996  WIPO.

OTHER PUBLICATIONS

C. Tomlin, ed., The Pesticide Manual, 10th ed. (1995) 351, 352, 831, 832, 1017, 1018.
Chem. Abst., vol. 85, No. 17, 117, 936f (1976).

Primary Examiner—Allen J. Robinson
Attorney, Agent, or Firm—Gabriel Lopez

[57] ABSTRACT

Plant-protecting active ingredient mixtures having synergistically enhanced action, wherein component I is a compound having plant-immunising action of formula I

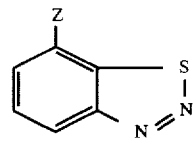

wherein Z is CN, COOH or a salt thereof, CO—OC$_1$—C$_4$alkyl or CO—SC$_1$—C$_4$alkyl;

and wherein component II is a compound selected from the group
A) 4-[3-(4-chlorophenyl)-3-(3,4-dimethoxyphenyl)acryloyl]morpholine ("dimethomorph");
B) 5-methyl-1,2,4-triazolo[3,4-b][1,3]benzothiazole ("tricyclazole"); and
C) 3-allyloxy-1,2-benzothiazole-1,1-dioxide ("probenazole").

7 Claims, No Drawings

CROP PROTECTION PRODUCTS

The present invention relates to novel plant-protecting active ingredient mixtures having synergistically enhanced action, comprising at least two active ingredient components together with a suitable carrier, wherein component I is a compound having plant-immunising action of formula I

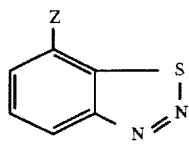

wherein Z is CN, COOH or a salt thereof, CO—O$C_1$—$C_4$alkyl or CO—S$C_1$—$C_4$alkyl;

and wherein component II is a commercial product selected from the group

A) 4-|3-(4-chlorophenyl)-3-(3,4-dimethoxyphenyl) acryloyl|morpholine ("dimethomorph"), (Reference: C. Tomlin (Editor): The Pesticide Manual, 10th edition, Farnham, UK, 1994, pages 351–352);

B) 5-methyl-1,2,4-triazolo|3,4-b||1,3|benzothiazole ("tricyclazole"), (Reference: C. Tomlin (Editor): The Pesticide Manual, 10th edition, Farnham, UK, 1994, pages 1017–1018); and C) 3-allyloxy-1,2-benzothiazole-1,1-dioxide ("probenazole"), (Reference: C. Tomlin (Editor): The Pesticide Manual, 10th edition, Farnham, UK, 1994, pages 831–832).

The invention relates also to salts and metal complexes of compounds I and II.

Of the compounds of formula I, preference is given to those wherein Z is COOH (compound IA) or a salt thereof, CN (compound IB), COO$CH_3$ (compound IC) or COS$CH_3$ (compound ID).

Preferred salts are alkali metal and alkaline earth metal salts, especially lithium, sodium, potassium, magnesium or calcium salts, and also organic salts, especially salts of salt-forming amines, for example trimethylamine, triethylamine, N,N-dimethylaniline, pyridine, triethanolamine, morpholine.

Very special preference is given to the compound of formula I wherein Z is COS$CH_3$ (compound ID).

It is known that compounds of formula I activate the plant's own latent defence system against pathogenic microbial influences and accordingly are able to protect the plant against pathogens (EP-A-313 512).

At low rates of application those compounds have no direct action on the noxious organisms, but they immunise the healthy plant against diseases.

The disadvantage in using compounds of formula I to control plant diseases is that the action is often inadequate at low rates of application.

Surprisingly, it has now been found that compounds of formula I in admixture with one of the conventional microbicides IIA to IIC have synergistically enhanced action. Using such mixtures it is possible to control plant diseases on the one hand by strengthening the plant by activating its own defence system and on the other hand by additionally controlling the pathogens directly. Compared with the customary methods of controlling plant diseases, unexpectedly small amounts of active ingredients are required.

A particular advantage of the mixtures according to the invention is further that, because the modes of action of components I and II are completely different, the threat of resistance being developed in the control of plant diseases is effectively prevented.

The synergistically enhanced action of mixtures of components I and II manifests itself, for example, in lower rates of application, a longer duration of action and altogether higher crop yields. Such enhancements were not to be expected from the sum of the actions of the individual components.

The present invention relates also to a method of protecting plants against plant diseases, especially against fungus infestation, by treating the plants, parts of the plants or their surroundings with a component I and a component II in any desired sequence or simultaneously.

Advantageous mixing ratios of the two active ingredients are

I:IIA=from 1:30 to 1:1, preferably I:II=from 1:30 to 1:3 and from 1:10 to 1:3.

I:IIB=from 1:20 to 1:1, preferably I:II=from 1:5 to 1:1 and from 1:2.5 to 1:1.

I:IIC=from 1:50 to 2:1, preferably I:II=from 1:25 to 1:1 and from 1:10 to 1:2.

The active ingredient mixtures I+II according to the invention have very advantageous properties for protecting plants against disease infestation.

The active ingredient mixtures of the invention can be used to inhibit or destroy the microorganisms which occur on plants or on parts of plants (the fruit, blossom, leaves, stems, tubers or roots) of different crops of useful plants, while at the same time parts of plants that grow later are also protected against such microorganisms. They can also be used as dressings in the treatment of plant propagation material, especially seed (fruit, tubers, grains) and plant cuttings (e.g. rice), to provide protection against fungus infections as well as against phytopathogenic fungi which occur in the soil. The active ingredient mixtures according to the invention are distinguished by the fact that they are especially well tolerated by plants and are environmentally friendly.

The active ingredient mixtures are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfect (e.g. Botrytis, Helminthosporium, Rhynchosporium, Fusarium, Septoria, Cercospora, Alternaria, Pyricularia and, especially, Pseudocercosporella herpotrichoides); Oomycetes (e.g. Phytophthora, Peronospora, Bremia, Pythium, Plasmopara).

Target crops for the areas of indication disclosed herein comprise within the scope of the present invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The active ingredient mixtures according to the invention are especially advantageous for use in vegetables, rice and tobacco; also in potatoes, vines, lawn areas and hops.

The mixtures are especially suitable as follows:

a) I+IIA for the treatment of vegetables and tobacco against Oomycetes, especially against Phytophthora, Peronospora, Bremia;
b) I+IIB for the treatment of rice against Fungi imperfecti, especially Pyricularia;
c) I+IIC for the treatment of rice against Fungi imperfecti, especially Pyricularia, and against bacterial diseases.

The mixtures of active ingredients of formulae I and II are generally used in the form of compositions. The active ingredients of formulae I and II can be applied to the area or plant to be treated either simultaneously or in succession on the same day, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers.

A preferred method of applying an active ingredient mixture comprising at least one of each of the active ingredients I and II is application to the parts of the plants that are above the soil, especially to the leaves (foliar application). The frequency and rate of application depend upon the biological and climatic living conditions of the pathogen. The active ingredients can, however, also penetrate the plant through the roots via the soil or via the water (systemic action) if the locus of the plant is impregnated with a liquid formulation (e.g. in rice culture) or if the substances are introduced in solid form into the soil, e.g. in the form of granules (soil application). In order to treat seed, the compounds of formulae I and II can also be applied to the seeds (coating), either by impregnating the tubers or grains with a liquid formulation of each of the active ingredients in succession, or by coating them with an already combined wet or dry formulation. In addition, in special cases, other methods of application to plants are possible, for example treatment directed at the buds or the fruit trusses.

The compounds of the combination are used in unmodified form or, preferably, together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are normally from 50 g to 2 kg a.i./ha, preferably from 100 g to 1000 g a.i./ha, especially from 250 g to 700 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the active ingredients of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g. phosphatidylethanolamine, phos- phatidylserine, phosphatidylglycerol and lysolecithin.

The agrochemical compositions generally comprise 0.1 to 99%, preferably 0.1 to 95%, of active ingredients of formulae I and II, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

The following Examples serve to illustrate the invention; in those Examples "active ingredient" denotes a mixture of compound I and compound II in a specific mixing ratio.

| Wettable powders | a) | b) | c) |
|---|---|---|---|
| active ingredient [I:II = 1:3(a), 1:2(b), 1:1(c)] | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:II = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [I:II = 1:6(a), 1:2(b), 1:10(c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:II = 2:1) | 15% |
| sodium lignosulfonate | 2% |
| carboxymethylcellulose | 1% |
| kaolin | 82% |

The active ingredient is mixed and g round with the adjuvants, and the mixture is moistened with water. The mixture is extruded and then dried in a stream of air.

| Coated granules | |
|---|---|
| active ingredient (I:II = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:II = 1:8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combinations". Weeds, Vol.15, pages 20–22; 1967):

ppm=milligrams of active ingredient (=a.i.) per litre of spray mixture

X=% action by active ingredient I using p ppm of active ingredient

Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.
O/E=synergy factor (SF).

In the Examples which follow, the infestation of the untreated plants is assumed to be 100%, which corresponds to an action of 0%.

Example B-1: Action against Phytophthora infestans on tomatoes a) Curative action After a cultivation period of 3 weeks, tomato plants of the "Red Gnome" variety are sprayed with a zoospore suspension of the fungus and incubated in a cabinet at 18° to 20° and 100% humidity. Humidification is stopped after 24 hours. When the plants have dried, they are sprayed with a mixture comprising the test compound formulated as a wettable powder in a concentration of 200 ppm. After the spray coating has dried, the plants are again placed in the humidity cabinet for 4 days. The activity of the test compounds is evaluated on the basis of the number and size of the typical leaf specks that have occurred after that time.

b) Preventive-systemic action

The test compound formulated as a wettable powder is applied in a concentration of 60 ppm (based on the volume of the soil) to the soil surface of three-week-old tomato plants of the "Red Gnome" variety planted in pots. After a 3-day waiting period, the undersides of the leaves of the plants are sprayed with a zoospore suspension of Phytophthora infestans. The plants are then kept in a spray cabinet for 5 days at 18° to 20° C. and 100% humidity. After that time, typical leaf specks form, the number and size of which are used to evaluate the activity of the test compounds.

In particular, mixtures of component IA or ID with IIA yield good results.

Example B-2: Action against Peronospora tabacina on tobacco plants

Tobacco plants (6 weeks old) are sprayed with a formulated solution of the test compound. Four days after treatment, the plants are inoculated with a sporangia suspension of the fungus, kept at high humidity for 4 to 5 days and then incubated further under a normal day/-night sequence.

Evaluation of the symptoms in the tests is based on the leaf surface infested with fungus. The infestation of the untreated plants corresponds to 0% action.

Component I: compound ID (benzothiadiazole-7-carboxylic acid thiomethyl ester)

Component II: compound IIA (dimethomorph)

| Test No. | mg a.i. per liter (ppm) | | | % action | | SF |
|---|---|---|---|---|---|---|
| | a.i. ID | a.i. IIA | I:II | O (found) | E (expected) | O/E |
| 1 | 0.03 | | | 14 | | |
| 2 | 0.1 | | | 34 | | |
| 3 | 0.3 | | | 88 | | |
| 4 | | 0.3 | | 52 | | |
| 5 | | 1 | | 52 | | |
| 6 | 0.03 | 1 | 1:33 | 74 | 59 | 1.3 |

-continued

| Test | mg a.i. per liter (ppm) | | % action | | SF |
|---|---|---|---|---|---|
| No. | a.i. ID | a.i. IIA | I:II | O (found) | E (expected) | O/E |
| 7 | 0.1 | 0.3 | 1:3 | 92 | 68 | 1.4 |
| 8 | 0.1 | 1 | 1:10 | 95 | 68 | 1.4 |

Example B-3: Action against Colletotrichum lagenarium on Cucumis sativus L.

a) After a cultivation period of 10 to 14 days, cucumber plants are sprayed with a spray mixture prepared from a wettable powder formulation of the test compound. After 3 to 4 days, the plants are infected with a spore suspension ($1.0 \times 10^5$ spores/ml) of the fungus and incubated for 30 hours at high humidity and a temperature of 23° C. Incubation is then continued at normal humidity and 22° C. to 23° C.

Evaluation of protective action is made 7 to 10 days after infection and is based on fungus infestation.

b) After a cultivation period of 10 to 14 days, cucumber plants are treated by soil application with a spray mixture prepared from a wettable powder formulation of the test compound. After 3 to 4 days, the plants are infected with a spore suspension ($1.5 \times 10^5$ spores/ml) of the fungus and incubated for 30 hours at high humidity and a temperature of 23° C. Incubation is then continued at normal humidity and 22° C.

Evaluation of protective action is made 7 to 10 days after infection and is based on fungus infestation.

In particular, mixtures of component IA or ID with IIA yield good results.

Example B-4: Action against Pyricularia oryzae on rice plants

Rice plants about 2 weeks old are placed together with the soil around the roots in a container filled with spray mixture. Fungus infestation is evaluated 36 days later. Infestation of the untreated plants corresponds to 0% action.

Component I: compound ID (benzothiadiazole-7-carboxylic acid thiomethyl ester)

Component II: compound IIB (tricyclazole)

| Test | mg a.i. per liter (ppm) | | % action | | SF |
|---|---|---|---|---|---|
| No. | a.i ID | a.i. IIB | I:II | O (found) | E (expected) | O/E |
| 1 | 0.5 | | | 65 | | |
| 2 | 0.25 | | | 39 | | |
| 3 | 0.1 | | | 18 | | |
| 4 | 0.05 | | | 5 | | |
| 5 | | 1 | | 74 | | |
| 6 | | 0.5 | | 71 | | |
| 7 | | 0.25 | | 48 | | |
| 8 | | 0.1 | | 32 | | |
| 9 | 0.25 | 0.25 | 1:1 | 75 | 68 | 1.1 |
| 10 | 0.1 | 0.25 | 1:2.5 | 69 | 57 | 1.2 |
| 11 | 0.1 | 0.1 | 1:1 | 61 | 44 | 1.4 |

-continued

| Test | mg a.i. per liter (ppm) | | % action | | SF |
|---|---|---|---|---|---|
| No. | a.i ID | a.i. IIB | I:II | O (found) | E (expected) | O/E |
| 12 | 0.05 | 1 | 1:20 | 80 | 75 | 1.1 |
| 13 | 0.05 | 0.25 | 1:5 | 58 | 50 | 1.2 |

What is claimed is:

1. A plant-protecting composition having synergistic action against disease infestation, comprising synergistic, fungicidally effective amounts of at least two active ingredient components together with a suitable carrier, wherein component I is a compound of formula I

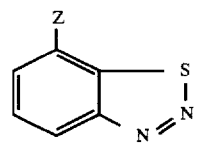

wherein Z is —CO—$SC_{1-4}$ alkyl
and wherein component II is

4-[3-(4-chlorophenyl)-3-(3,4-dimethoxyphenyl)acryloyl] morpholine wherein the ratio by weight of I:II is from 1:30 to 1:1.

2. A composition of claim 1 wherein Z is —CO—$SCH_3$ and the ratio is from 1:20 to 1:1.

3. A composition of claim 2 wherein the ratio is from 1:10 to 1:3.

4. A method of protecting plants against plant diseases by treating, in any desired sequence or simultaneously, the plants, parts of the plants, or their surroundings with synergistic, fungicidally effective amounts of a component I which is a compound of formula I

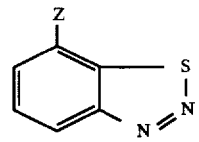

wherein Z is —CO—$SC_{1-4}$ alkyl
and of a component II which is

4-[3-(4-chlorophenyl)-3-(3,4-dimethoxyphenyl)acryloyl] morpholine wherein the ratio by weight of I:II is from 1:30 to 1:1.

5. A method of claim 4, wherein Z is —CO—$SCH_3$ and the ratio is from 1:20 to 1:1.

6. A method of claim 5 wherein the ratio if from 1:10 to 1:3.

7. A method of claim 4 wherein the plants are vegetables or tobacco.

* * * * *